United States Patent
Steidl et al.

(10) Patent No.: US 10,941,209 B2
(45) Date of Patent: Mar. 9, 2021

(54) IDENTIFICATION AND USE OF NEW TUMOR-PROMOTING GENE IN HEMATOLOGICAL MALIGNANCIES

(71) Applicants: Albert Einstein College of Medicine, Bronx, NY (US); British Columbia Cancer Agency Branch, Vancouver (CA)

(72) Inventors: Ulrich Steidl, New Rochelle, NY (US); Christian Steidl, North Vancouver (CA); Ujunwa Cynthia Okoye-Okafor, Bronx, NY (US)

(73) Assignees: Albert Einstein College of Medicine, Bronx, NY (US); British Columbia Cancer Agency Branch, Vancouver (CA)

( * ) Notice: Subject to any disclaimer, the term of this patent is extended or adjusted under 35 U.S.C. 154(b) by 293 days.

(21) Appl. No.: 16/040,877

(22) Filed: Jul. 20, 2018

(65) Prior Publication Data

US 2018/0371105 A1 Dec. 27, 2018

Related U.S. Application Data

(63) Continuation of application No. 14/442,906, filed as application No. PCT/US2013/070227 on Nov. 15, 2013, now abandoned.

(60) Provisional application No. 61/727,419, filed on Nov. 16, 2012, provisional application No. 61/740,485, filed on Dec. 21, 2012.

(51) Int. Cl.
| | |
|---|---|
| *C12N 15/113* | (2010.01) |
| *C07K 16/32* | (2006.01) |
| *G01N 33/574* | (2006.01) |
| *C12Q 1/6886* | (2018.01) |

(52) U.S. Cl.
CPC ............ *C07K 16/32* (2013.01); *C12N 15/113* (2013.01); *C12Q 1/6886* (2013.01); *G01N 33/57426* (2013.01); *C07K 2317/30* (2013.01); *C12N 2310/14* (2013.01); *C12N 2310/531* (2013.01); *C12N 2320/30* (2013.01); *C12Q 2600/136* (2013.01); *C12Q 2600/158* (2013.01); *G01N 2500/04* (2013.01); *G01N 2500/10* (2013.01)

(58) Field of Classification Search
CPC ........................... C12N 15/113; C12N 2310/14
See application file for complete search history.

(56) References Cited

U.S. PATENT DOCUMENTS

| | | |
|---|---|---|
| 5,910,486 A | 6/1999 | Curiel |
| 8,715,674 B2 | 5/2014 | Zeng |

| | | |
|---|---|---|
| 2007/0083334 A1 | 4/2007 | Mintz et al. |
| 2007/0099251 A1 | 5/2007 | Zhang et al. |
| 2013/0203058 A1 | 8/2013 | Shuber |

FOREIGN PATENT DOCUMENTS

| | | | |
|---|---|---|---|
| WO | WO-2008109492 A1 * | 9/2008 | ......... C12N 15/1138 |
| WO | 2012021845 A2 | 2/2012 | |
| WO | 2012113064 A1 | 8/2012 | |

OTHER PUBLICATIONS

PCT International Search Report and Written Opinion, dated Mar. 18, 2014 in connection with PCT International Application. No. PCT/US2013/70227, 14 pages.
Wen H et al., entitled "New fusion transcripts identified in normal karyotype acute myeloid leukemia,1" PLoS One, 2012 vol. 7, No. 12, pp. e51203, pp. 1-10.
NP_001185713, NCBI Reference Sequence: NP_001185713.1, Uncharacterized Protein LOC145788[*Homo sapiens*], Oct. 27, 2012, 1 page.
Steidl U et al., entitled "MHC class II transactivator CIIT is a recurrent gene fusion partner in lymphoid cancers," Nature, Mar. 17, 2011, vol. 471, No. 7338, pp. 377-381.
Steidl U et al., entitled "A distal single nucleotide polymorphism alters long-range regulation of the PU.1 gene in acute myeloid leukemia," J Clin Invest, Sep. 2007, vol. 117, No. 9, pp. 2611-2620.
Xia J et al., entitled "NGS Catalog: A Database of Next Generation Sequencing Studies in Humans," Human Mutation Database in Brief 33: E2341-E2355, 2012.
Vardiman J W, entitled "The World Health Organization (WHO) classification of tumors of the hematopietic and lymphoid tissues: An overview with emphasis on the myeloid neoplasms," Chem Biol Interact, Mar. 19, 2010, vol. 184, No. 1-2, pp. 16-20.
Banerjee D, entitled "Recent Insights into the Biology of Hodgkin's Lymphoma," Hodgkin's LymphomaIntech, Mar. 2012, pp. 4-26.
Okoye-Okafor U C et al., entitled "Molecular and Funtcional Characterization of the Novel Protein-Coding Gene Tihl (Translocated in Hodgkin's Lymphoma) in Hematopoiesis," Blood, Oct. 21, 2013, vol. 122, No. 21, abstract, 2 pages.
Chan and Carter, Nature Reviews Immunology, 10:301-316 (Year: 2010).
Imai and Takaoka, Nat Rev Cancer 6:714-727 (Year: 2006).
Carter, P J, Nat. Rev Immunol 6:343-357 (Year: 2006).
Chames et al., Br. J Pharmacol. 157:220-233 (Year: 2009).
Ruggeri et al., Biochem Pharmacol 87:150-161 (Year: 2014).
Dao T et al., Sci. Tansl. Med., 5(176): pp. 1-22, 2013.
Wang Y et al., Molecular Oncology 9: 1982-1993,2015.
Kinsinger L S et al., Ann Intern. Med. 137: 59-67, 2002.
Violette P D et al., J Am. Board Fam. Med., 25: 111-119, 2012.
Jordan M S et al., Nature Immunology, 4: 110-116, 2003.
Hoelzer D, Curro Opin. Oncol., 25: 701-706, 2013.

\* cited by examiner

*Primary Examiner* — Brian Whiteman
(74) *Attorney, Agent, or Firm* — Fox Rothschild LLP

(57) ABSTRACT

Methods are provided for diagnosing and treating a blood cancer or a myelodysplastic syndrome in a subject. Associated compositions and kits therefor are also provided.

3 Claims, 14 Drawing Sheets

Specification includes a Sequence Listing.

IDENTIFICATION AND USE OF NEW TUMOR-PROMOTING GENE IN HEMATOLOGICAL MALIGNANCIES

CROSS-REFERENCE TO RELATED APPLICATIONS

This application is a continuation of U.S. Ser. No. 14/442,906, which is a U.S. national stage under 35 U.S.C. § 371 of PCT International Patent Application No. PCT/US2013/070227, filed Nov. 15, 2013, which claims benefit of U.S. Provisional Application No. 61/727,419, filed Nov. 16, 2012, and of U.S. Provisional Application No. 61/740,485, filed Dec. 21, 2012, the contents of each of which are hereby incorporated by reference.

INCORPORATION-BY-REFERENCE OF MATERIAL SUBMITTED VIA EFS-WEB

The ASCII text file titled "Sub Sequence Listing" having a file size of 20.7 KB and created on Sep. 22, 2020 is hereby incorporated by reference in its entirety.

BACKGROUND OF THE INVENTION

Throughout this application various publications are referred to. Full citations for these references may be found at the end of the specification. The disclosures of these publications, and of all patents, patent application publications and books referred to herein, are hereby incorporated by reference in their entirety into the subject application to more fully describe the art to which the subject invention pertains.

The hypothetical gene locus BX648577 (FLJ27352/hypothetical LOC145788) was recently identified as part of a gene fusion with Class II Transactivator (CIITA) in Hodgkin's lymphoma using whole-transcriptome paired-end sequencing (Steidl C. et al., Nature 2011). While CIITA has been extensively studied, it is not known whether BX648577 is a gene (whether it is transcribed and expressed physiologically as a protein and whether it has a biological function).

The present invention addresses the need for novel anti-leukemia treatments, antibodies useful in treating or diagnosing leukemias, and related assays based on discoveries disclosed herein regarding BX648577.

SUMMARY OF THE INVENTION

A method is provided of treating a cancer in a subject comprising administering to the subject an agent which inhibits expression of a BX648577 gene, or an agent which inhibits activity of an expression product of a BX648577 gene, so as to thereby treat the cancer.

Also provided is a method of diagnosing a subject as likely to develop a cancer or a myelodysplastic syndrome, or as susceptible to developing a cancer or a myelodysplastic syndrome, comprising determining whether a sample obtained from the subject expresses a BX648577 gene at a level in excess of a predetermined control level, wherein BX648577 gene expressed in the sample determined to be in excess of the predetermined control level indicates that the subject is likely to develop the cancer or is susceptible to developing the cancer, or is likely to develop the myelodysplastic syndrome or is susceptible to developing the myelodysplastic syndrome.

Also provided is a method of treating a cancer in a subject or inhibiting development of a cancer in a subject comprising determining whether a sample obtained from the subject expresses a BX648577 gene at a level in excess of a predetermined control level, wherein BX648577 gene expressed in the sample determined to be in excess of the predetermined control level identifies the subject as having the cancer or as likely to develop the cancer, and administering to a subject so-identified an anti-cancer therapy so as to thereby treat the cancer or inhibit development of a cancer.

An isolated antibody directed against the translocated in Hodgkin's lymphoma (TIHL) protein comprising SEQ ID NO:1 is also provided, as well as isolated antigen-binding fragments of such antibody, as are compositions comprising the isolated antibody. A cDNA encoding SEQ ID NO:1 is also provided.

Also provided is a kit comprising written instructions and reagents for determining TIHL levels or BX648577 gene (TIHL gene) expression levels in a biological sample obtained from a subject for determining the subject's susceptibility to a hematological malignancy.

An isolated protein is provided comprising consecutive amino acid residues having the sequence set forth in SEQ ID NO:1.

DETAILED DESCRIPTION OF THE INVENTION

Figure 1:
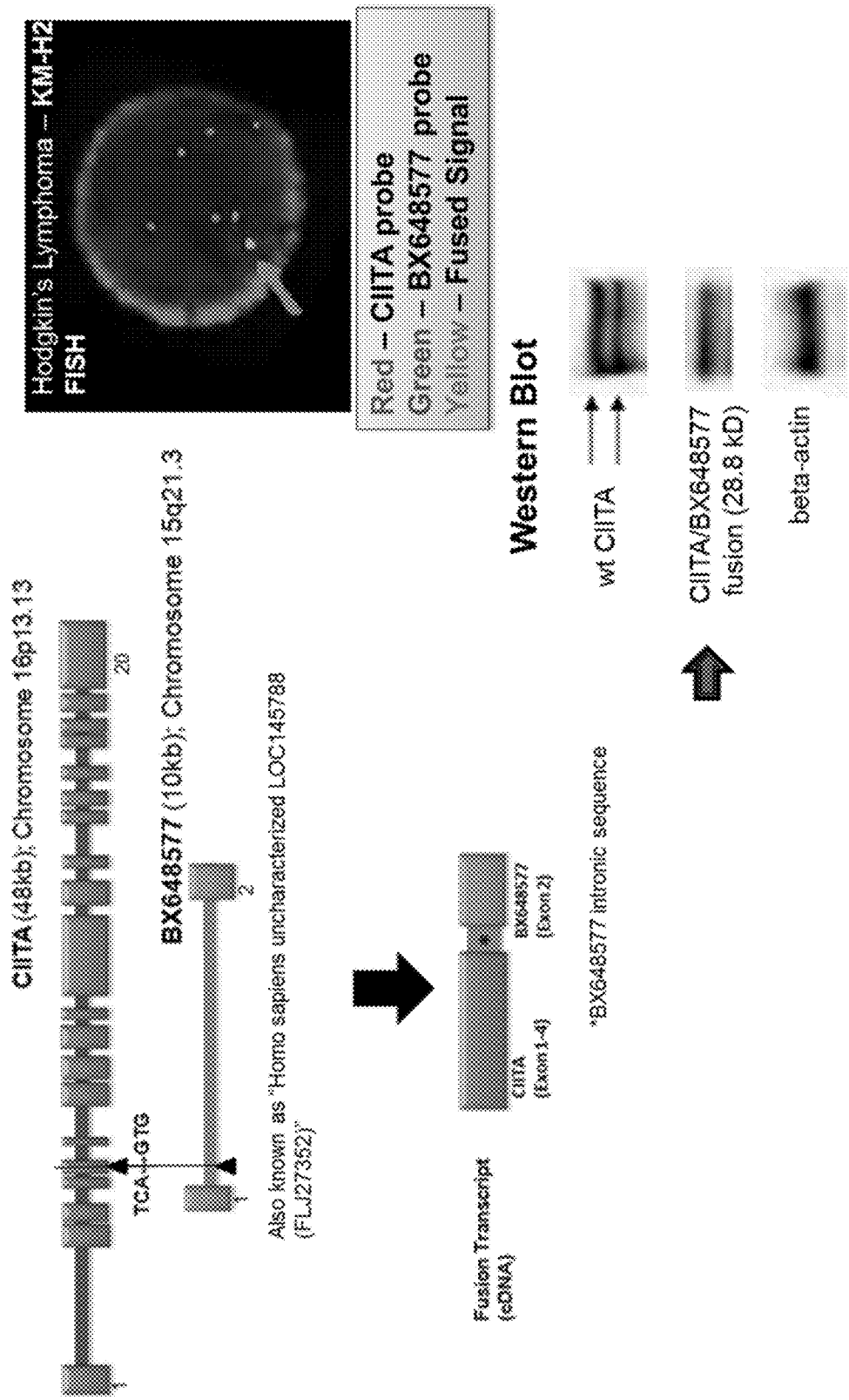
FIG. 1: Confirmation of protein existence was performed by Western blot analysis of the 28 kilodalton protein. The protein encoded by the full length gene was given the name Translocated in Hodgkin's Lymphoma (TIHL) and the gene encoding it named TIHL.

A method is provided of treating a cancer in a subject comprising administering to the subject an agent which inhibits expression of a BX648577 gene, or an agent which inhibits activity of an expression product of a BX648577 gene, so as to thereby treat the cancer.

Also provided is a method of diagnosing a subject as likely to develop a cancer or a myelodysplastic syndrome, or as susceptible to developing a cancer or a myelodysplastic syndrome, comprising determining whether a sample obtained from the subject expresses a BX648577 gene at a level in excess of a predetermined control level, wherein BX648577 gene expressed in the sample determined to be in excess of the predetermined control level indicates that the subject is likely to develop the cancer or is susceptible to developing the cancer, or is likely to develop the myelodysplastic syndrome or is susceptible to developing the myelodysplastic syndrome. In an embodiment, the method is for diagnosing a subject as likely to develop a cancer. In an embodiment, the method is for diagnosing a subject as susceptible to developing a cancer. In an embodiment, the method is for diagnosing a subject as likely to develop a myelodysplastic syndrome. In an embodiment, the method is for diagnosing a subject as susceptible to developing a myelodysplastic syndrome. In an embodiment, the cancer is a hematological cancer.

Also provided is a method of treating a cancer in a subject or inhibiting development of a cancer in a subject comprising determining whether a sample obtained from the subject expresses a BX648577 gene at a level in excess of a predetermined control level, wherein BX648577 gene expressed in the sample determined to be in excess of the predetermined control level identifies the subject as having the cancer or as likely to develop the cancer, and administering to a subject so-identified an anti-cancer therapy so as to thereby treat the cancer or inhibit development of a cancer. In an embodiment, the method is of treating a cancer in a subject and the subject has the cancer. In an embodiment, the method is of inhibiting development of a cancer in a subject and the subject does not yet have the cancer.

In an embodiment of the methods, the cancer is a hematological malignancy. In an embodiment of the methods, the hematological malignancy is an acute myeloid leukemia.

In an embodiment of the methods, the anti-cancer therapy is an anti-acute myeloid leukemia therapy. In an embodiment of the methods, the anti-cancer therapy is agent which inhibits expression of a BX648577 gene, or an agent which inhibits activity of an expression product of a BX648577 gene. In an embodiment of the methods, the agent comprises an anti-translocated in Hodgkin's lymphoma protein (TIHL) antibody or an antigen-binding fragment of an anti-TIHL antibody.

In an embodiment of the methods, determining the level of expression of the BX648577 gene is effected by quantifying gene RNA transcript levels. In an embodiment, RNA transcript levels are quantified using quantitative reverse transcriptase PCR. In an embodiment, the agent is an siRNA directed to the BX648577 gene or an shRNA directed to the BX648577 gene. In an embodiment, the agent is an siRNA directed to a nucleic acid encoding BX648577 gene product or a transcript thereof or a shRNA directed to a nucleic acid encoding BX648577 gene product or a transcript thereof.

In an embodiment of the methods, the BX648577 gene encodes an mRNA encoding SEQ ID NO:1.

In an embodiment of the methods, the sample comprises a blood sample, a sample derived from blood, a bone marrow sample, or a stem cell.

Also provided is an isolated antibody directed against the THIL comprising SEQ ID NO: 1. Also provided is an isolated antigen-binding fragment of antibody directed against the THIL comprising SEQ ID NO:1. The isolated antigen-binding fragment binds to THIL comprising SEQ ID NO:1. Also provided is a cDNA encoding SEQ ID NO:1.

In an embodiment, the antibody is a monoclonal antibody. In an embodiment, the antibody is a human antibody, a humanized antibody or a chimeric antibody. In an embodiment, the antibody fragment is a fragment of a human antibody, a humanized antibody or a chimeric antibody.

Also provided is a composition comprising any of the instant antibodies or fragments. In an embodiment, the composition comprises a physiological carrier. In an embodiment, the composition comprises a pharmaceutically acceptable carrier. In an embodiment, the composition comprises the isolated antibody conjugated to a cyotoxin, a radioisotope, a chemotherapeutic or an imaging label or comprises the isolated antigen-binding fragment of the antibody conjugated to a cyotoxin, a radioisotope, a chemotherapeutic or an imaging label. Imaging labels are well known in the art and include fluorophores and fluorescent dyes and radio-opaque dyes.

Also provided is a kit comprising written instructions and reagents for determining THIL levels or BX648577 gene expression levels in a biological sample obtained from a subject for determining the subject's susceptibility to a hematological malignancy. In an embodiment, the hematological malignancy is a leukemia. In an embodiment, the hematological malignancy is AML. In an embodiment, the hematological malignancy is myelodysplastic syndrome.

In an embodiment, the kit comprises a microarray having (i) an antibody specific for THIL or (ii) a nucleic acid probe thereon specific for a transcript of an BX648577 gene.

In an embodiment, the kit comprises a set of forward and reverse PCR primers specific for a region of the BX648577 gene comprising a portion encoding a transcript of the BX648577 gene for which the nucleic acid probe is specific.

An isolated protein is provided comprising consecutive amino acid residues having the sequence set forth in SEQ ID NO:1. In an embodiment, the isolated protein consists of amino acid residues having the sequence set forth in SEQ ID NO:1.

In an embodiment in humans TIHL comprises the sequence:

(SEQ ID NO: 1)
MTDRNRDKKSTSPSNSDTEMKSEQLPPCVNPGNPVFSCMLDPKTLQTATS

LSKPQQMIMYKTNSSHYGEFLPIPQFFPCNYTPKEQVFSSHIRATGFYQN

NTLNTAPDRTRTLDFPPNIQHTL.

A cDNA encoding SEQ ID NO:1 is also provided.

In an embodiment of the methods, RNA transcript levels are quantified using quantitative reverse transcriptase PCR.

In an embodiment of the methods, the cancer is an acute myeloid leukemia. In an embodiment, the aggressive anti-cancer therapy is an anti-acute myeloid leukemia therapy. In an embodiment, the subject has been diagnosed as being of intermediate cytogenetic risk for AML. An aggressive anti-cancer therapy is determined by those of skill in the art, such as physicians, based on the cancer, and means that a less-aggressive anti-cancer therapy is available. For example, aggressive anti-cancer therapy in AML could comprise a stem-cell transplantation. For example, an aggressive anti-cancer therapy in could comprise an aggressive chemotherapy.

In an embodiment of the methods, the sample comprises a blood sample, a bone marrow sample, or a stem cell.

In an embodiment, the kits comprise a plurality of sets of forward and reverse PCR primers, each set specific for a region of one of the recited genes comprising a portion encoding a transcript of the gene for which the nucleic acid probe is specific.

In an embodiment, an siRNA (small interfering RNA) used as an agent in the methods or compositions described herein is directed to BX648577 gene (which encodes TIHL) and comprises a portion which is complementary to an mRNA sequence corresponding to the following:

(SEQ ID NO: 2)
acttccagttgctatggttacgagttgcaacctccagaaagaattcgtggt ttcacccgggaaaacagctccccggattaaacggataggtttacacatac tgatccaccagctattcatcttctgtttgctgctttaattgggtgcggt taaaaggccacgtccctaggcgttcaccggctttcttgccatctgctgca tgaaaactgactttgccgaaaaaattaacaaagaagagcgaaaatgacag accgcaaccgggataagaaaagtacttcaccttcaaattcagacacagaa atgaaatctgaacaactgcctccttgtgtgaaccctggcaatcctgtgtt ttcatgtatgttggatccaaagacactccagacagccacctcactatcaa aacctcaaatgattatgtataaaaccaattcaagtcattatggtgaatt ctacctattccacagtttttcccctgcaattatactccaaaggagcaagt attttcaagccatatcagagcaactggattttatcaaaataacactctaa atactgcacctgacagaaccagaactcttgattttcctaatattcaacac actctatgaaaatatattcctttgtatattgaagagaaaatatactcggg aaaaatgagtgttaaatctaagggtagaatacctaataaagaagataaaa agttttgaatcaattttaaaataagttaaataaagtatttcaactgata aaaaaaaaaaaaaaaaaaaaaaaaaaaaaaa
and the siRNA is effective to inhibit expression of
TIHL.

In an embodiment, the siRNA comprises a double-stranded portion (duplex). In an embodiment, the siRNA is 20-25 nucleotides in length. In an embodiment the siRNA comprises a 19-21 core RNA duplex with a one or 2 nucleotide 3' overhang on, independently, either one or both strands. In an embodiment, the overhang is UU. The siRNA can be 5' phosphorylated or not and may be modified with any of the known modifications in the art to improve efficacy and/or resistance to nuclease degradation. In a non-limiting embodiment, the siRNA can be administered such that it is transfected into one or more cells.

In one embodiment, a siRNA of the invention comprises a double-stranded RNA comprising a first and second strand, wherein one strand of the RNA is 80, 85, 90, 95 or 100% complementary to a portion of an RNA transcript of a gene encoding TIHL. Thus, in an embodiment, the invention encompasses an siRNA comprising a 19, 20 or 21 nucleotide first RNA strand which is 80, 85, 90, 95 or 100% complementary to a 19, 20 or 21 nucleotide portion, respectively, of an RNA transcript of an TIHL-encoding gene. In an embodiment, the second RNA strand of the double-stranded RNA is also 19, 20 or 21 nucleotides, respectively, a 100% complementary to the first strand. In another embodiment, a siRNA of the invention comprises a double-stranded RNA wherein one strand of the RNA comprises a portion having a sequence the same as a portion of 18-25 consecutive nucleotides of an RNA transcript of a gene encoding Homo sapiens TIHL. In yet another embodiment, a siRNA of the invention comprises a double-stranded RNA wherein both strands of RNA are connected by a non-nucleotide linker. Alternately, a siRNA of the invention comprises a double-stranded RNA wherein both strands of RNA are connected by a nucleotide linker, such as a loop or stem loop structure.

In one embodiment, a single strand component of a siRNA of the invention is from 14 to 50 nucleotides in length. In another embodiment, a single strand component of a siRNA of the invention is 14, 15, 16, 17, 18, 19, 20, 21, 22, 23, 24, 25, 26, 27, or 28 nucleotides in length. In yet another embodiment, a single strand component of a siRNA of the invention is 21 nucleotides in length. In yet another embodiment, a single strand component of a siRNA of the invention is 22 nucleotides in length. In yet another embodiment, a single strand component of a siRNA of the invention is 23 nucleotides in length. In one embodiment, a siRNA of the invention is from 28 to 56 nucleotides in length.

In another embodiment, an siRNA of the invention comprises at least one 2'-sugar modification. In another embodiment, an siRNA of the invention comprises at least one nucleic acid base modification. In another embodiment, an siRNA of the invention comprises at least one phosphate backbone modification.

In one embodiment, RNAi inhibition of TIHL is effected by an agent which is a short hairpin RNA ("shRNA"). The shRNA is introduced into the cell by transduction with a vector. In an embodiment, the vector is a lentiviral vector. In an embodiment, the vector comprises a promoter. In an embodiment, the promoter is a U6 or H1 promoter. In an embodiment the shRNA encoded by the vector is a first nucleotide sequence ranging from 19-29 nucleotides complementary to the target gene, in the present case TIHL. In an embodiment the shRNA encoded by the vector also comprises a short spacer of 4-15 nucleotides (a loop, which does not hybridize) and a 19-29 nucleotide sequence that is a reverse complement of the first nucleotide sequence. In an embodiment the siRNA resulting from intracellular processing of the shRNA has overhangs of 1 or 2 nucleotides. In an embodiment the siRNA resulting from intracellular processing of the shRNA overhangs has two 3' overhangs. In an embodiment the overhangs are UU.

In one embodiment, inhibition of TIHL is effected by an agent which is an antibody or by a fragment of an antibody. As used herein, the term "antibody" refers to complete, intact antibodies, "antigen-binding fragment of an antibody" refers to Fab, Fab', F(ab)$_2$, and other fragments thereof, or an ScFv, which bind the antigen of interest, in this case TIHL. Complete, intact antibodies include, but are not limited to, monoclonal antibodies such as murine monoclonal antibodies, polyclonal antibodies, chimeric antibodies, human antibodies, and humanized antibodies.

Various forms of antibodies may be produced using standard recombinant DNA techniques (Winter and Milstein, Nature 349: 293-99, 1991). For example, "chimeric" antibodies may be constructed, in which the antigen binding domain from an animal antibody is linked to a human constant domain (an antibody derived initially from a non-human mammal in which recombinant DNA technology has been used to replace all or part of the hinge and constant regions of the heavy chain and/or the constant region of the light chain, with corresponding regions from a human immunoglobulin light chain or heavy chain) (see, e.g., Cabilly et al., U.S. Pat. No. 4,816,567; Morrison et al., Proc. Natl. Acad. Sci. 81: 6851-55, 1984). Chimeric antibodies reduce the immunogenic responses elicited by animal antibodies when used in human clinical treatments. In addition, recombinant "humanized" antibodies may be synthesized. Humanized antibodies are antibodies initially derived from a nonhuman mammal in which recombinant DNA technology has been used to substitute some or all of the amino acids not required for antigen binding with amino acids from corresponding regions of a human immunoglobulin light or heavy chain. That is, they are chimeras comprising mostly human immunoglobulin sequences into which the regions responsible for specific antigen-binding have been inserted (see, e.g., PCT patent application WO 94/04679). Animals are immunized with the desired antigen, the corresponding antibodies are isolated and the portion of the variable region sequences responsible for specific antigen binding are removed. The animal-derived antigen binding regions are then cloned into the appropriate position of the human antibody genes in which the antigen binding regions have been deleted. Humanized antibodies minimize the use of heterologous (inter-species) sequences in antibodies for use in human therapies, and are less likely to elicit unwanted immune responses. Primatized antibodies can be produced similarly.

Another embodiment of the antibodies employed in the compositions and methods of the invention is a human antibody directed against TIHL, or a fragment of such antibody, which can be produced in nonhuman animals, such as transgenic animals harboring one or more human immunoglobulin transgenes. Such animals may be used as a source for splenocytes for producing hybridomas, for example as is described in U.S. Pat. No. 5,569,825.

Fragments of the antibodies described herein and univalent antibodies may also be used in the methods and compositions of this invention. Univalent antibodies comprise a heavy chain/light chain dimer bound to the Fc (or stem) region of a second heavy chain. "Fab region" refers to those portions of the chains which are roughly equivalent, or analogous, to the sequences which comprise the Y branch portions of the heavy chain and to the light chain in its entirety, and which collectively (in aggregates) have been shown to exhibit antibody activity. A Fab protein includes aggregates of one heavy and one light chain (commonly known as Fab'), as well as tetramers which correspond to the two branch segments of the antibody Y, (commonly known as F(ab)$_2$), whether any of the above are covalently or non-covalently aggregated, so long as the aggregation is capable of specifically reacting with a particular antigen or antigen family.

In an embodiment, the agents of the invention as described herein are administered in the form of a composition comprising the agent and a carrier. The term "carrier" is used in accordance with its art-understood meaning, to refer to a material that is included in a pharmaceutical composition but does not abrogate the biological activity of pharmaceutically active agent(s) that are also included within the composition. Typically, carriers have very low toxicity to the animal to which such compositions are to be administered. In some embodiments, carriers are inert.

In one embodiment of the methods, the TIHL expression level is detected using a detectable agent. As used herein, a "detectable agent" is any agent that binds to BX648577 gene or to TIHL and which can be detected or observed, when bound, by methods known in the art. In non-limiting examples, the detectable agent can be an antibody or a fragment of an antibody, which is itself detectable, e.g. by a secondary antibody, or which is labeled with a detectable marker such as a radioisotope, a fluorophore, a dye etc. permitting detection of the presence of the bound agent by the appropriate machine, or optionally in the case of visually detectable agents, with the human eye. In an embodiment, the amount of detectable agent can be quantified.

As used herein, a "cancer" is a disease state characterized by the presence in a subject of cells demonstrating abnormal uncontrolled replication. In a preferred embodiment, the cancer is a leukemia. In a most preferred embodiment, the cancer is acute myeloid leukemia. As used herein, "treating" a cancer, or a grammatical equivalent thereof, means effecting a reduction of, amelioration of, or prevention of further development of one or more symptoms of the disease, or placing the cancer in a state of remission, or maintaining it in a state of remission.

As used herein a "leukemia" is an art-recognized cancer of the blood or bone marrow characterized by an abnormal increase of immature white blood cells called "blasts". The specific condition of acute myeloid leukemia (AML) is a cancer of the myeloid line of blood cells, characterized by the rapid growth of abnormal white blood cells that accumulate in the bone marrow and interfere with the production of normal blood cells.

In an embodiment, the stem cell obtained from the subject is obtained by obtaining a sample from the subject. As used herein, a "sample" of a cancer or of a tumor is a portion of the cancer or of the tumor, respectively, for example as obtained by a biopsy. In the case of a leukemia, or AML, the preferred sample is bone marrow, or is derived from bone marrow, or is blood or is derived from blood. In an embodiment, the sample is, or comprises, a stem cell or a progenitor cell. As used herein a "sample derived from blood" or a "sample derived from bone marrow" is a sample which has been treated chemically and/or mechanically, but in such a manner not to alter TIHL expression levels or activity levels which might be contained therein.

In an embodiment, the microarray comprises probes attached via surface engineering to a solid surface by a covalent bond to a chemical matrix (via, in non-limiting examples, epoxy-silane, amino-silane, lysine, polyacrylamide). Suitable solid surface can be, in non-limiting examples, glass or a silicon chip, a solid bead forms of, for example, polystyrene. As used herein, unless otherwise specified, a microarray includes both solid-phase microarrays and bead microarrays. In an embodiment, the microarray is a solid-phase microarray. In an embodiment, the microarray is a plurality of beads microarray. In an embodiment, the microarray is a spotted microarray. In an embodiment, the microarray is an oligonucleotide microarray. The nucleic acid probes (e.g. oligonucleotide probes) of the microarray may be of any convenient length necessary for unique discrimination (is specific for) of target gene transcripts. In non-limiting examples, the probes are 20 to 30 nucleotides in length, 31 to 40 nucleotides in length, 41 to 50 nucleotides in length, 51 to 60 nucleotides in length, 61 to 70 nucleotides in length, or 71 to 80 nucleotides in length. In an embodiment, the target sample (e.g. gene mRNA transcripts), or nucleic acids derived from the target sample, such as cDNA, are contacted with a detectable marker, such as one or more fluorophores, under conditions permitting the detectable marker to attach to the target sample or nucleic acids derived from the target sample. Such fluorophores are well known in the art, for example cyanine 3, cyanine 5. In an embodiment, the target hybridized to the probe can be detected by conductance, mass spectrometry (including MALDI-TOF), or electrophoresis. The microarray can be manufactured by any method known in the art including by photolithography, pipette, drop-touch, piezoelectric (ink-jet), and electric techniques.

If desired, mRNA in the sample can be enriched with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or Sephadex™ (see Ausubel et al., CURRENT PROTOCOLS IN MOLECULAR BIOLOGY, vol. 2, Current Protocols Publishing, New York (1994), hereby incorporated by reference). In a non-limiting example, once bound, poly(A)+ mRNA is eluted from the affinity column using 2 mM EDTA/0.1% SDS. Methods for preparing total and poly(A)+ RNA are well known and are described generally in Sambrook et al., MOLECULAR CLONING—A LABORATORY MANUAL (2ND ED.), Vols. 1-3, Cold Spring Harbor Laboratory, Cold Spring Harbor, N.Y. (1989)) and Ausubel et al., CURRENT PROTOCOLS IN MOLECULAR BIOLOGY, vol. 2, Current Protocols Publishing, New York (1994)), the contents of both of which are incorporated herein. RNA may be isolated from samples of eukaryotic cells by procedures that involve lysis of the cells and denaturation of the proteins contained therein. Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., Biochemistry 18:5294-5299 (1979) hereby incorporated by reference). Poly(A)+ RNA can be selected by selection with oligo-dT cellulose (see Sambrook et al, MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol. If desired, RNase inhibitors may be added to the lysis buffer. Likewise, for certain cell types, it may be desirable to add a protein denaturation/digestion step to the protocol.

In an embodiment of the methods and compositions the BX648577 gene is human. In an embodiment of the methods and compositions the BX648577 gene product is human.

As used herein "likely" in describing an occurrence means more likely than not. As used herein, "susceptible to" in describing a condition means more likely to develop the condition in a situation than a majority of the population from which the subject is drawn.

As used herein a "predetermined level" with regard to a quantity is the level of the quantity determined from one or more suitable control(s). In an embodiment the suitable control is a subject who does not have the relevant cancer and/or is not susceptible to the relevant cancer, or is a tissue or cell of such a subject. In an embodiment, the cancer that the subject does not have and/or is not susceptible to is acute myeloid leukemia.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Initial comparative analysis of the 13-16 kDa predicted BX648577 (TIHL) protein sequences in various species revealed high evolutionary conservation (≥54%), including in invertebrates (e.g. *Saccoglossus kowalevskii*). A TIHL (BX648577)-specific antibody generated was used to identify endogenous protein expression of TIHL by western blot analysis in several cell lines, including 293T cells, and myeloid NB4 and KG1a cells. Expression analysis was performed in several leukemia and lymphoma cell lines by quantitative reverse transcription-polymerase chain reaction (qRT-PCR). It was found that TIHL mRNA was widely and variably expressed, with particularly high expression in malignant hematopoietic cells including 5 fold increase in NB4 cells ($p=0.0057$) and 9 fold higher in THP-1 cells ($p=8.66e-6$, when compared to healthy donor peripheral blood CD14+ monocytes. In addition, TIHL mRNA expression was detectable in sorted, primary human and murine bone marrow derived hematopoietic stem cells (Lin-CD34+ CD38- (human) or Lin-c-Kit+Sca-1+ (mouse)) and progenitor cells (Lin-CD34+CD38+ (human) or Lin-c-Kit+Sca-1- (mouse)), as well as human healthy donor mature peripheral blood mononuclear cells with the most prominent expression in Glycophorin A and CD56 positive cells by qRT-PCR. Utilizing murine HPC-7 cells as well as acute myeloid leukemia cell lines (NB4, KG1a), the biological consequences of modulating TIHL expression was assessed. Knockdown of TIHL by two independent shRNAs with greater than 50% knockdown efficiencies, led to significantly decreased leukemic cell growth in suspension culture. Additionally we observed decreased clonogenic capacity in both cell lines when the cells were transduced with either TIHL sh#1 or sh#2, with 72% ($p=1.19e-3$) and 77% ($p=8.36e-4$) inhibition in clonogenicity in NB4 cells when compared to cells transduced with a non-silencing control vector. Similarly, 72% ($p=7.13e-4$) and 63% ($p=7.78e-4$) inhibition of clonogenicity was observed in KG1a cells. In addition, knockdown of TIHL led to decreased cell cycling with less EdU incorporation in KG1a and NB4 cells, as well as increased cell death. No changes indicative of differentiation were found when cellular morphology and surface protein expression was analyzed. Cloning of the full length cDNA of human TIHL into a lentiviral expression vector was performed. While ectopic expression of human or murine TIHL in sorted Lin-c-Kit+ cells did not lead to a change in clonogenicity when compared to the empty control vector, we observed a 1.5 fold (p=0.0161) and 2 fold (p=0.0039) increase in colony forming capacity in NB4 and murine HPC-7 cells respectively upon TIHL overexpression. For Empty or TIHL overexpressing NB4 cells grown in suspension culture, we observed approximately a 2 fold increase in cell growth (p<0.001). Finally, in silico domain analysis suggests that TIHL may function as an adaptor protein and may be involved in facilitating previously established signal transduction pathways.

Figure 2:
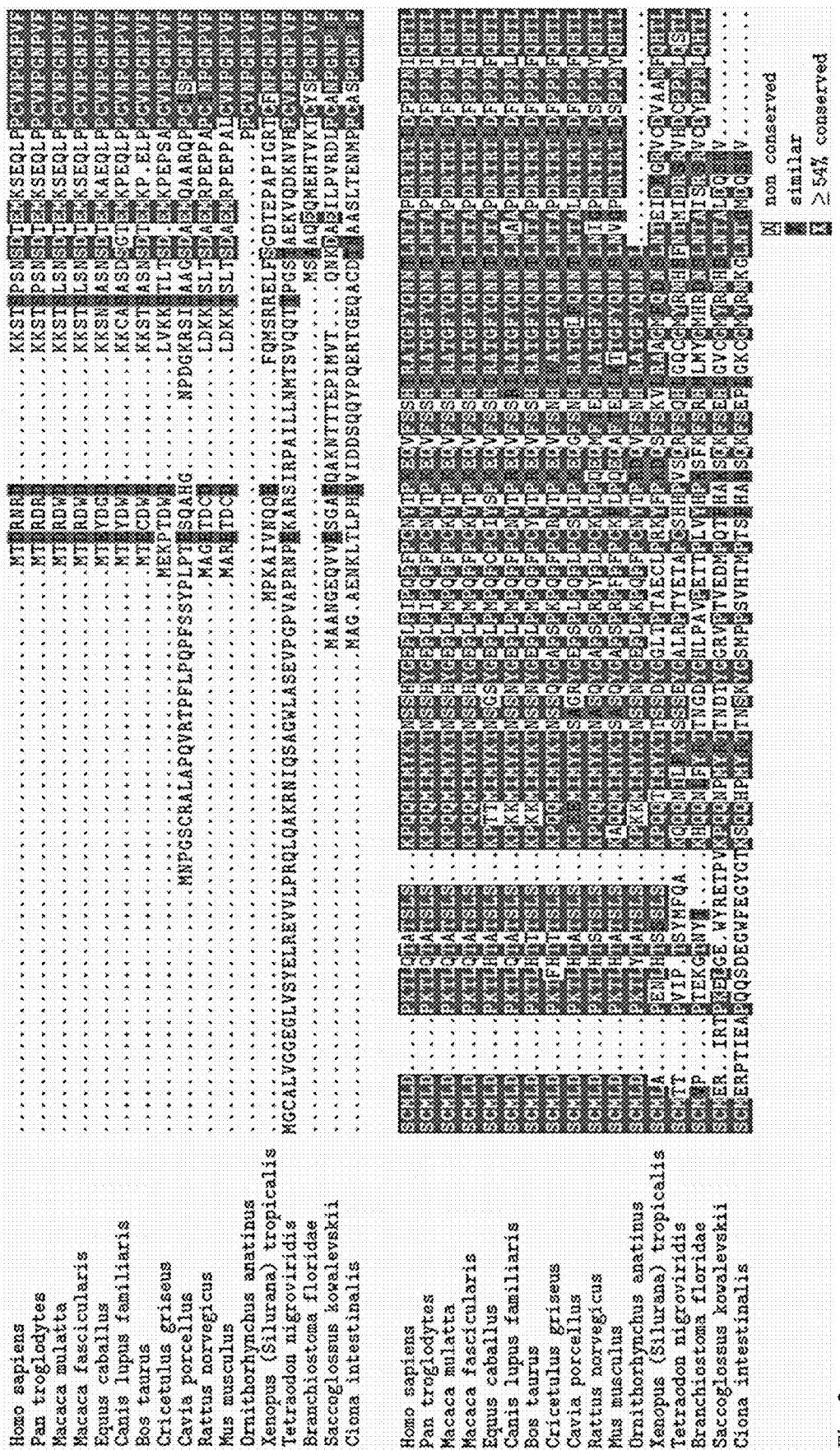
FIG. 2: The TIHL sequence was determined, and was found to be highly conserved across species. The amino acid sequences of the TIHL species have, in descending order, the sequences of SEQ ID NOs: 1, 3, 4, 5, 6, 7, 8, 9, 10, 11, 12, 13, 14, 15, 16, 17, and 18.
Figure 3:
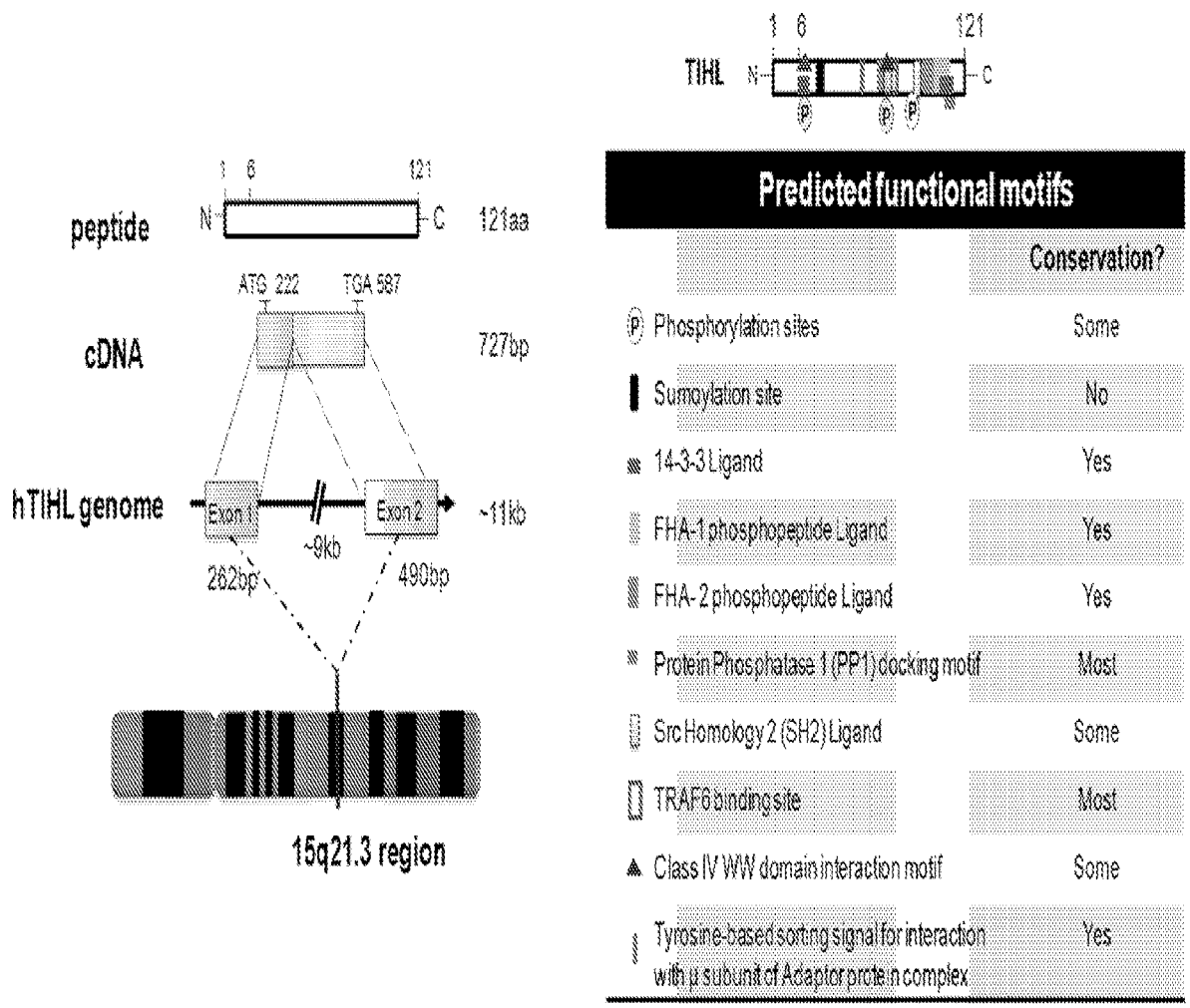
FIG. 3: Human TIHL was investigated for its genomic organization and predicted motifs. Potential roles were considered to be as an adaptor protein, signal transduction and/or localization regulation.

With regard to the figures herein: initially, BX648577 was identified as part of a novel hypothetical gene fusion in Hodgkin's Lymphoma cell line KM-H2. It was identified as co-localized CIITA and BX648577 on chromosome 16. Confirmation was performed by Western blot analysis of the 28 kilodalton fusion protein (see FIG. 1). The Wildtype full length BX648577 protein was given the name Translocated in Hodgkin's Lymphoma (TIHL). Subsequently, its actual physiological expression was investigated as well as any possible biological function. Both normal and malignant hematopoietic cells were used for this investigation. Its sequence was determined, and was found to be highly conserved across species (FIG. 2). Human TIHL was investigated for its genomic organization and predicted motifs (see FIG. 3). Potential roles were considered to be as an adaptor protein, signal transduction and/or regulated localization.

Figure 4:
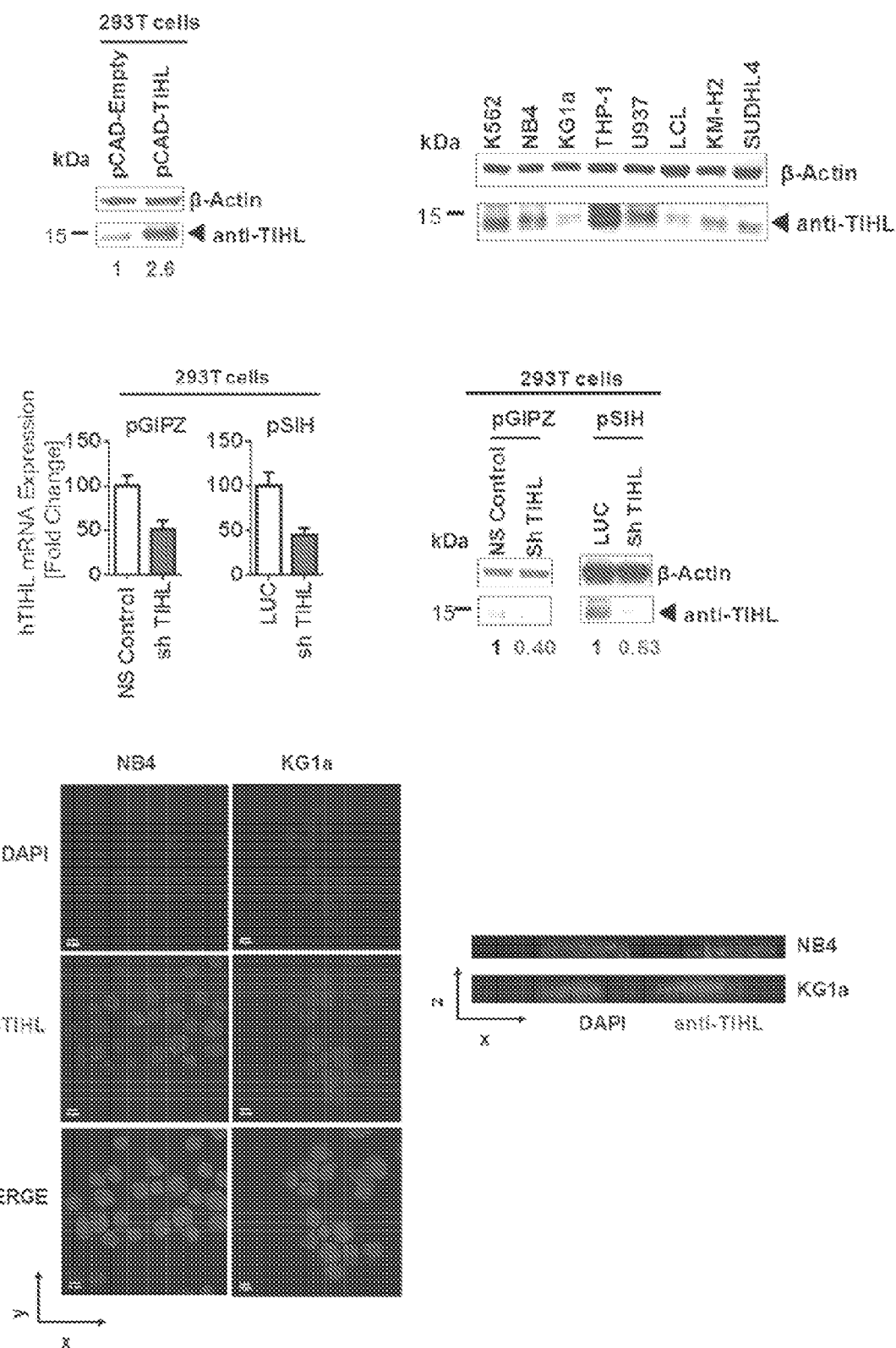
FIG. 4: The potential endogenous protein expression and localization was investigated. A TIHL specific antibody was generated to specifically probe its expression. Upon its overexpression by transfection using the lentiviral construct or knockdown shRNA constructs, we detect overexpression and downregulation of the endogenous proteins respectively in 293T cells. The antibody detects endogenous expression of the protein within various leukemia and lymphoma cell lines. Using immunofluorescence imaging coupled to confocal microscopy we detect both cytoplasmic and nuclear localization of the endogenous protein in NB4 and KG1a cells.

The potential endogenous protein expression and localization was investigated (FIG. 4). In investigating its possible role in hematopoiesis, the following questions were considered: is TIHL expressed in immature stem and progenitor cells of the bone marrow? (human & mouse) and in human peripheral blood mature cells; and is BX648577 aberrantly expressed in leukemias or lymphomas? Also investigated was the functional consequences of TIHL overexpression or knockdown in human hematopoietic cells.

Figure 5:
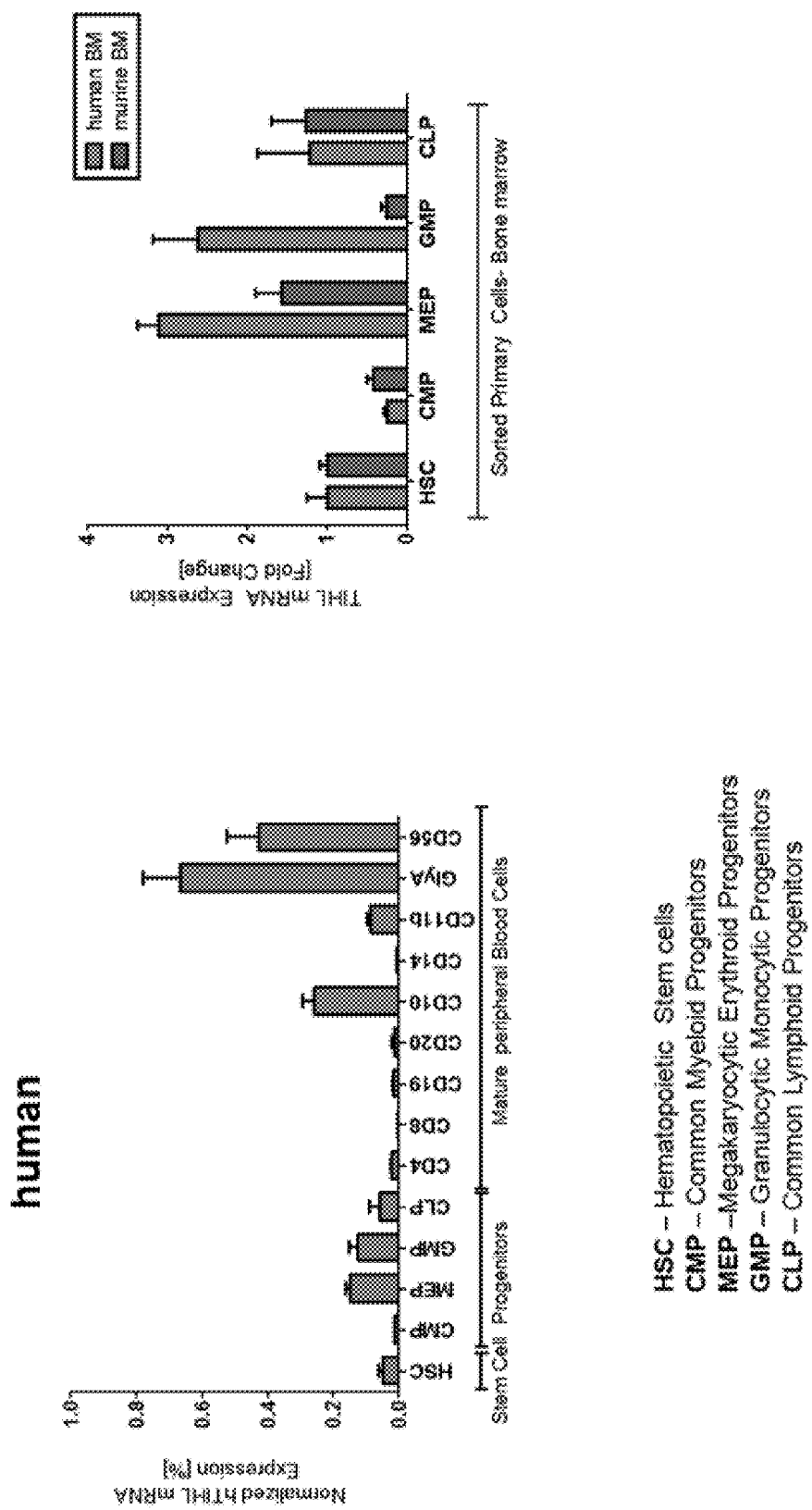
FIG. 5: TIHL mRNA expression was investigated in hematopoietic cells from human and murine bone marrow.
Figure 6:
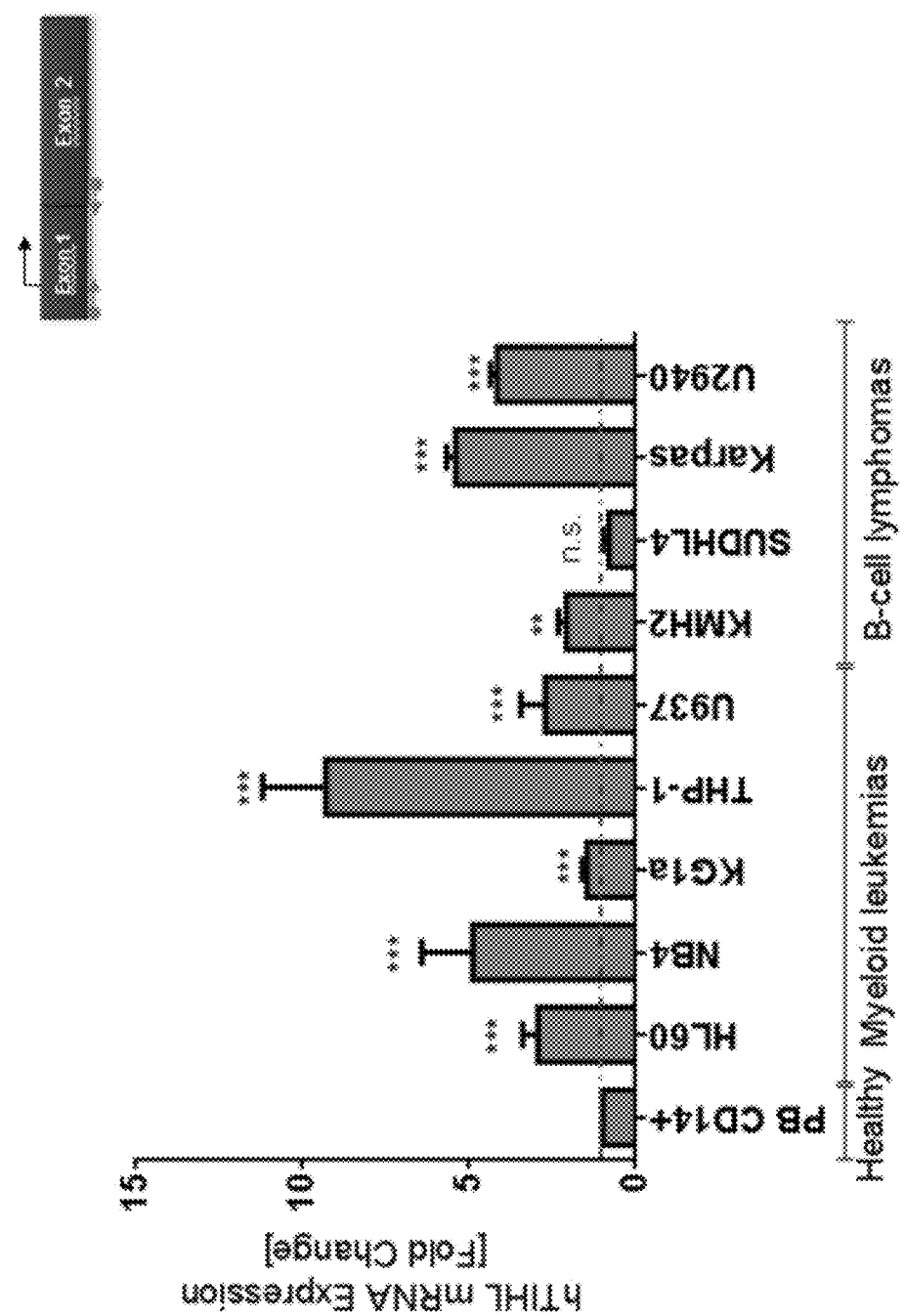
FIG. 6: TIHL mRNA expression profiles in leukemia and lymphoma cell lines were determined using realtime PCR primers specific to wild-type BX648577 expression.
Figure 7:
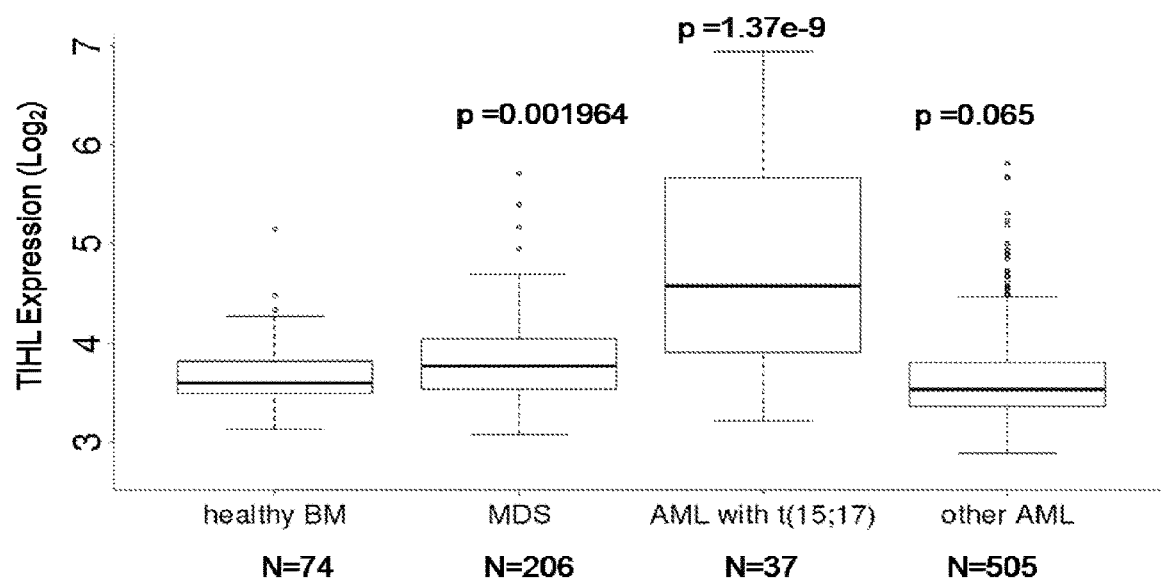
FIG. 7: Significant overexpression of TIHL was identified in patients with AML having translocation 15;17 (and in myelodysplastic syndromes (MDS)) compared to healthy controls and other AMLs.

TIHL mRNA expression was investigated in hematopoietic cells (FIG. 5). Then, TIHL mRNA expression profiles in leukemia and lymphoma cell lines were determined (FIG. 6) using real-time PCR primers specific to wild-type BX648577 expression. In addition, significant overexpression of BX648577 was identified in patients with AML having translocation 15;17 (and in MDS) compared to healthy controls and other AMLs (FIG. 7).

Figure 8:
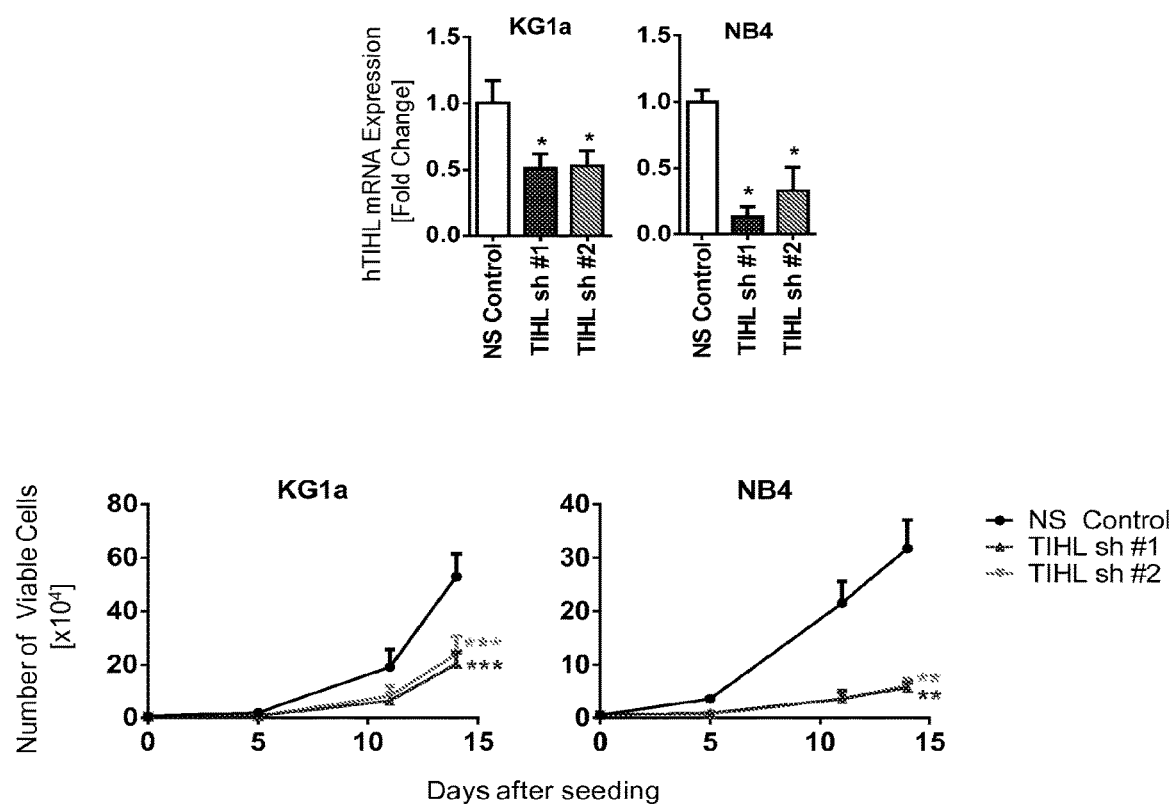
FIG. 8: Functional consequences of TIHL knockdown were investigated. Knockdown of TIHL in myeloid leukemia NB4 and KG1a cells inhibits cell growth.
Figure 9:
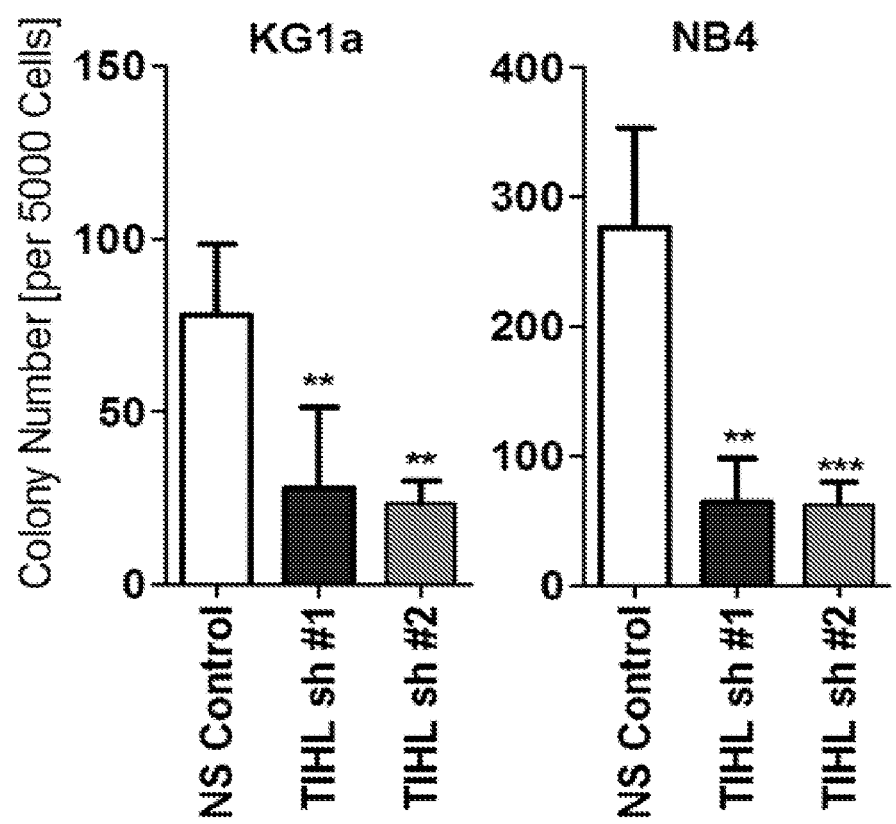
FIG. 9: Knockdown of TIHL in myeloid leukemia cells leads to decreased clonogenicity.
Figure 10:
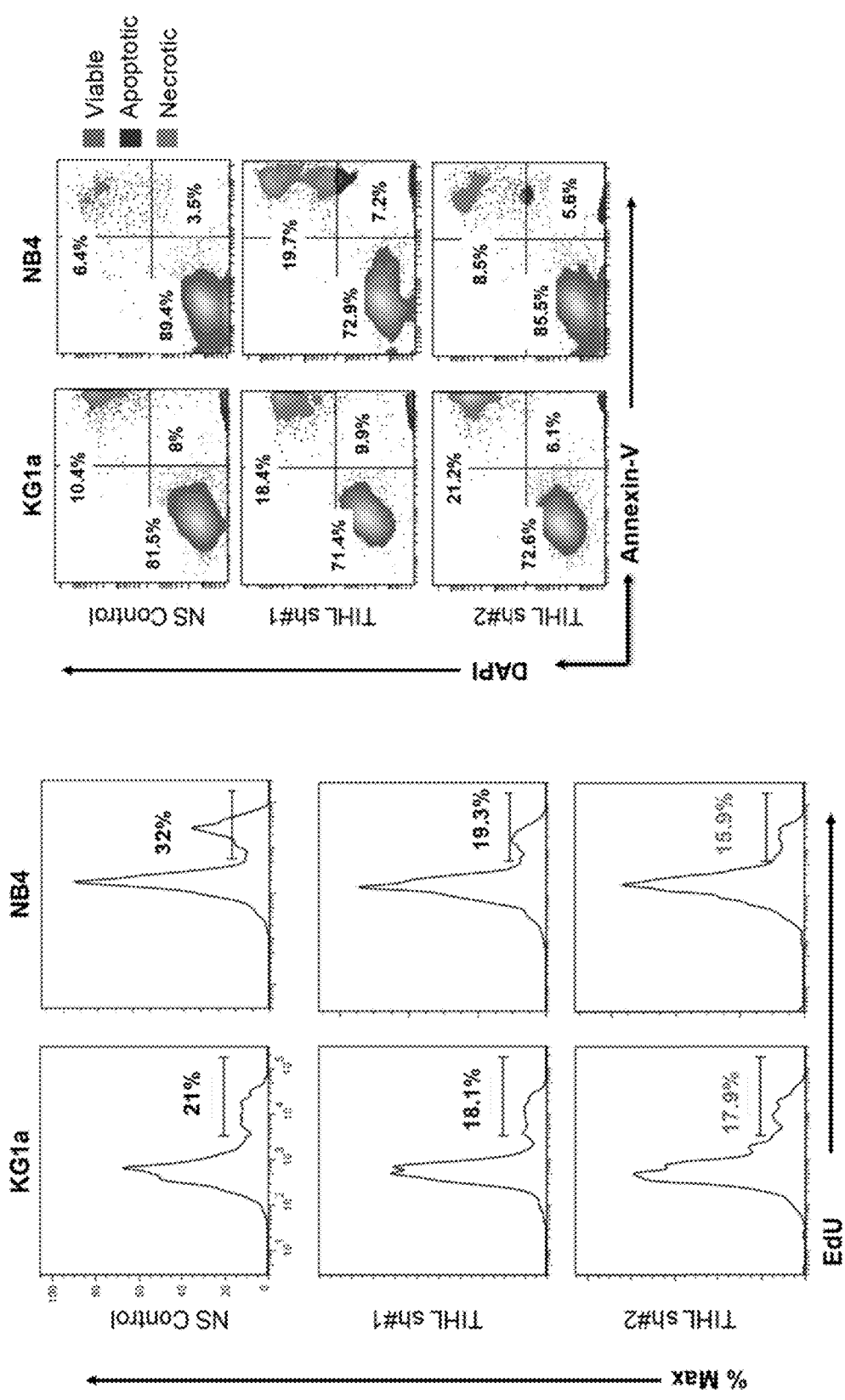
FIG. 10: Decreased cell cycle shown as decreased EdU incorporation and increased apoptosis with TIHL knockdown was observed in KG1a and NB4 cells.

Functional consequences of T1HL knockdown or overexpression were investigated. Knockdown of TIHL in myeloid leukemia NB4 and KG1a cells inhibits cell growth (FIG. 8). Knockdown of TIHL in myeloid leukemia cells also leads to decreased clonogenicity (FIG. 9). In TIHL knockdown in NB4 cells, no differences in colony morphology or size. Decreased EdU incorporation and increased apoptosis was observed with TIHL knockdown in KG1a and NB4 cells (FIG. 10).

Figure 11:
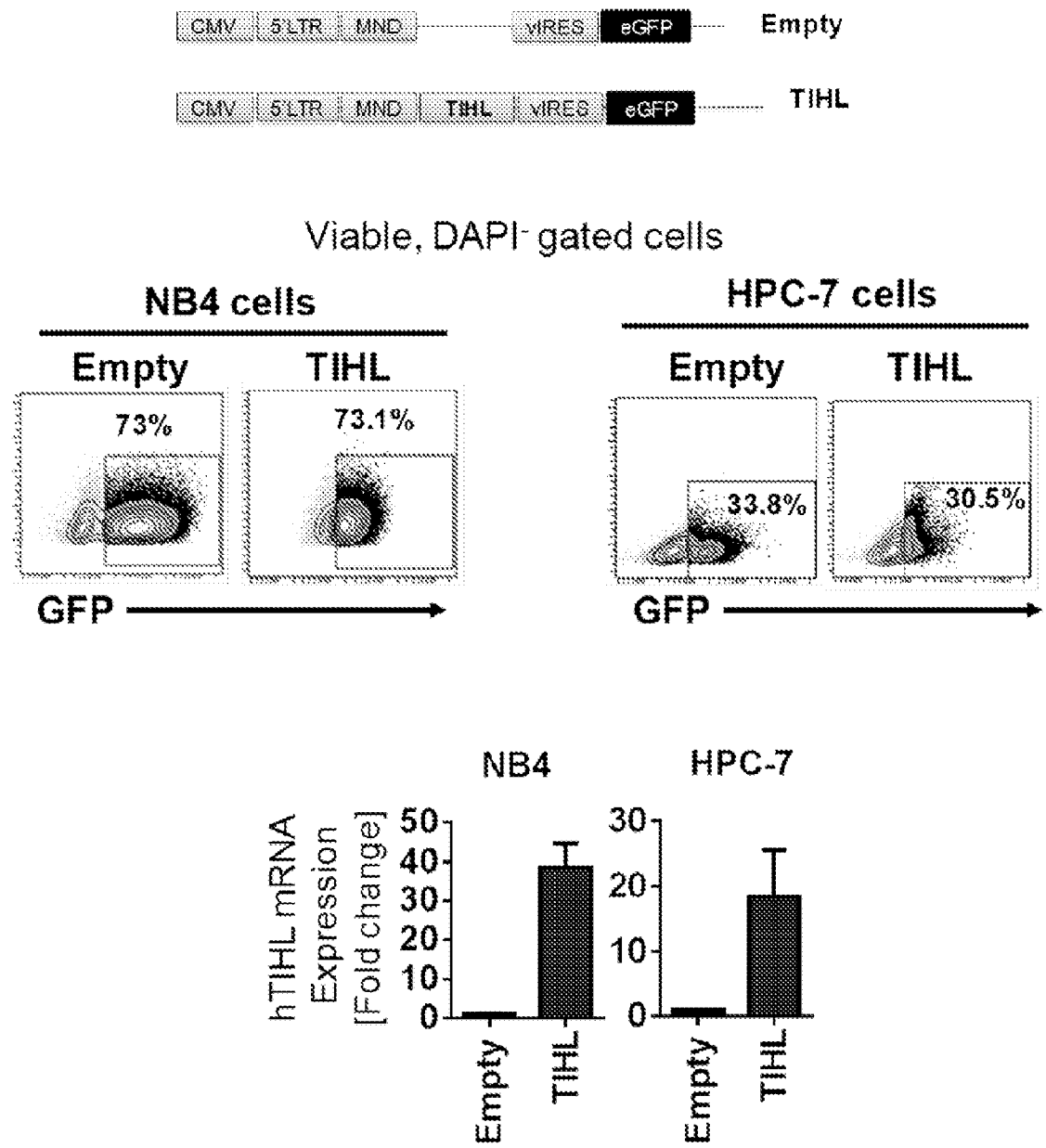
FIG. 11: Overexpression of Wildtype TIHL in human NB4 cells and murine HPC-7 cells. FACS plot of sorted cells and real time PCR show overexpression of TIHL RNA and protein (GFP).
Figure 12:
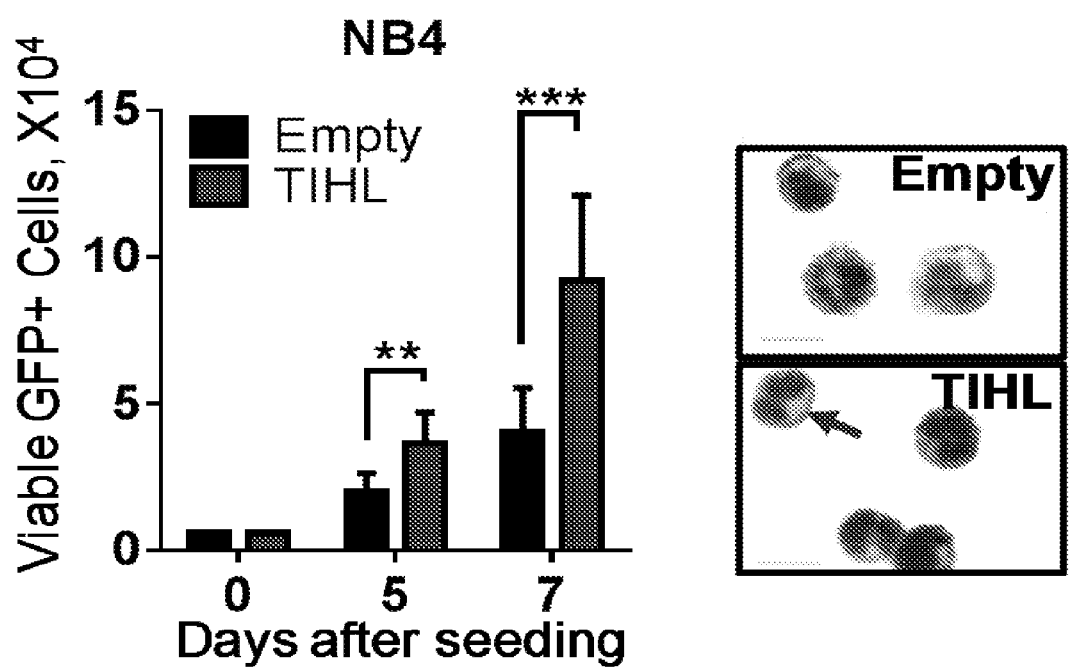
FIG. 12: TIHL overexpression confers a growth advantage in myeloid leukemia NB4 cells. Red arrow depicts a dividing cell.
Figure 13:
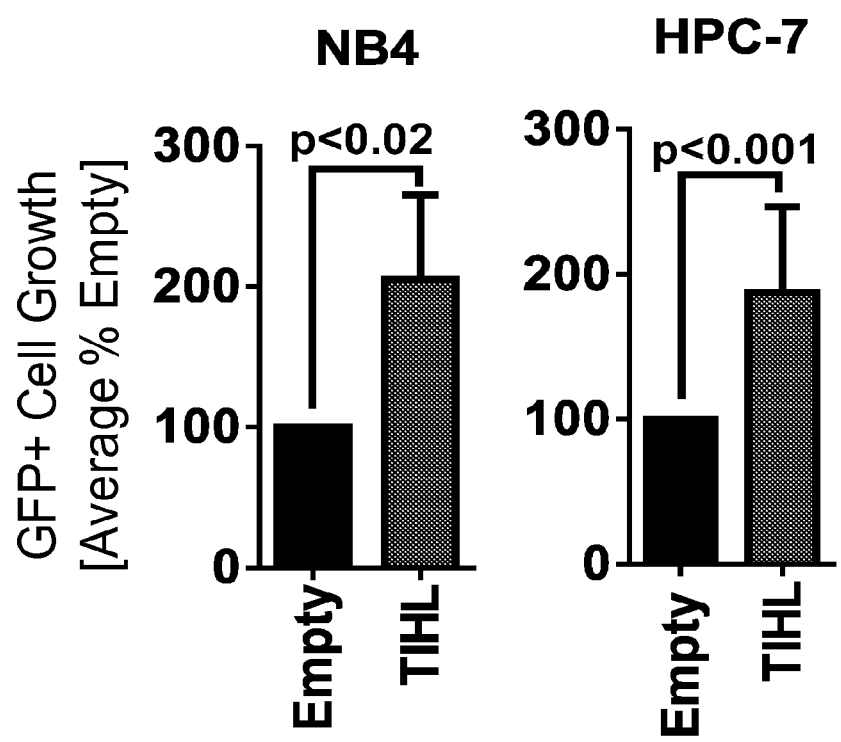
FIG. 13: TIHL overexpression leads to increased clonogenicity in human myeloid leukemia NB4 cells and murine HPC-7 cells.
Figure 14:
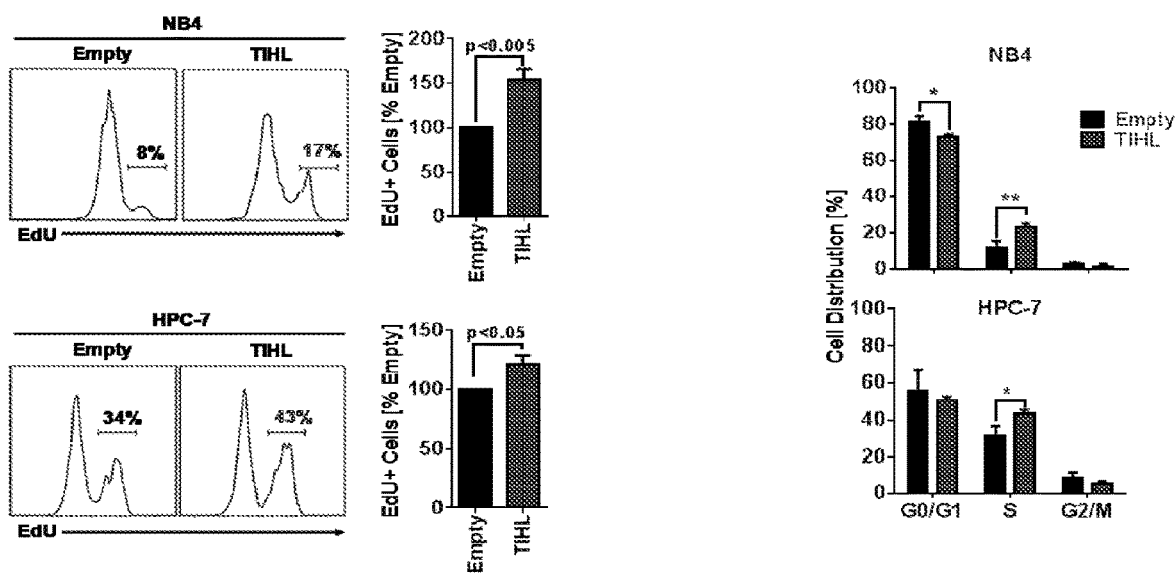
FIG. 14: TIHL overexpression leads increased cell cycling in both human myeloid leukemia NB4 and murine HPC-7 cells.

The effect of the overexpression of wildtype TIHL on NB4 and HPC-7 cells was also evaluated (FIG. 11). TIHL overexpression confers a growth advantage in myeloid leukemia NB4 cells (FIG. 12). TIHL overexpression also leads to increased clonogenicity in myeloid leukemia NB4 cells and murine HPC-7 cells (FIG. 13). TIHL overexpression also leads increased cell cycling (FIG. 14).

What is claimed is:

1. A method of treating a hematological malignancy in a subject comprising administering to the subject an amount of an agent which inhibits expression of a BX648577 gene, or an amount of an agent which inhibits activity of an expression product of a BX648577 gene, so as to thereby treat the hematological malignancy, wherein the agent is an siRNA directed to a BX648577 gene or an RNA transcript thereof, or an shRNA directed to a BX648577 gene or an RNA transcript thereof.

2. The method of claim 1, wherein the hematological malignancy is an acute myeloid leukemia.

3. The method of claim 1, wherein the BX648577 gene encodes an mRNA encoding a protein having the sequence of SEQ ID NO: 1.

* * * * *

SEQUENCE LISTING

<160> NUMBER OF SEQ ID NOS: 18

<210> SEQ ID NO 1
<211> LENGTH: 123
<212> TYPE: PRT
<213> ORGANISM: Homo sapiens

<400> SEQUENCE: 1

```
Met Thr Asp Arg Asn Arg Asp Lys Lys Ser Thr Ser Pro Ser Asn Ser
1               5                   10                  15

Asp Thr Glu Met Lys Ser Glu Gln Leu Pro Pro Cys Val Asn Pro Gly
            20                  25                  30

Asn Pro Val Phe Ser Cys Met Leu Asp Pro Lys Thr Leu Gln Thr Ala
        35                  40                  45

Thr Ser Leu Ser Lys Pro Gln Gln Met Ile Met Tyr Lys Thr Asn Ser
    50                  55                  60

Ser His Tyr Gly Glu Phe Leu Pro Ile Pro Gln Phe Phe Pro Cys Asn
65                  70                  75                  80

Tyr Thr Pro Lys Glu Gln Val Phe Ser Ser His Ile Arg Ala Thr Gly
                85                  90                  95

Phe Tyr Gln Asn Asn Thr Leu Asn Thr Ala Pro Asp Arg Thr Arg Thr
            100                 105                 110

Leu Asp Phe Pro Pro Asn Ile Gln His Thr Leu
            115                 120
```

<210> SEQ ID NO 2
<211> LENGTH: 782
<212> TYPE: DNA

<213> ORGANISM: Homo sapiens

<400> SEQUENCE: 2

```
acttccagtt gctatggtta cgagttgcaa cctccagaaa gaattcgtgg tttcacccgg      60
gaaacagct ccccggatta aacggatagg tttacacata ctgatccacc cagctattca     120
tcttctgttt gctgctttaa ttgggtgcgg ttaaaaggcc acgtccctag gcgttcaccg     180
gctttcttgc catctgctgc atgaaaactg actttgccga aaaattaac aaagaagagc      240
gaaaatgaca daccgcaacc gggataagaa aagtacttca ccttcaaatt cagacacaga    300
aatgaaatct gaacaactgc ctccttgtgt gaaccctggc aatcctgtgt tttcatgtat    360
gttggatcca aagacactcc agacagccac ctcactatca aaacctcaaa tgattatgta    420
taaaaccaat tcaagtcatt atggtgaatt tctacctatt ccacagttt tcccctgcaa     480
ttatactcca aaggagcaag tattttcaag ccatatcaga gcaactggat tttatcaaaa    540
taacactcta atactgcac ctgacagaac cagaactctt gattttccta atattcaaca     600
cactctatga aaatatattc ctttgtatat tgaagagaaa atatactcgg gaaaatgag    660
tgttaaatct aagggtagaa tacctaataa agaagataaa agttttgaa tcaattttta      720
aaataagtta aataaagtat ttcaactgat aaaaaaaaa aaaaaaaaa aaaaaaaaa       780
aa                                                                   782
```

<210> SEQ ID NO 3
<211> LENGTH: 123
<212> TYPE: PRT
<213> ORGANISM: Pan troglodytes

<400> SEQUENCE: 3

```
Met Thr Asp Arg Asp Arg Asp Lys Lys Ser Thr Ser Pro Ser Asn Ser
1               5                   10                  15
Asp Thr Glu Met Lys Ser Glu Gln Leu Pro Pro Cys Val Asn Pro Gly
                20                  25                  30
Asn Pro Val Phe Ser Cys Met Leu Asp Pro Lys Thr Leu Gln Thr Ala
            35                  40                  45
Thr Ser Leu Ser Lys Pro Gln Gln Met Ile Met Tyr Lys Thr Asn Ser
        50                  55                  60
Ser His Tyr Gly Glu Phe Leu Pro Ile Pro Gln Phe Phe Pro Cys Asn
65                  70                  75                  80
Tyr Thr Pro Lys Glu Gln Val Phe Ser Ser His Ile Arg Ala Thr Gly
                85                  90                  95
Phe Tyr Gln Asn Asn Thr Leu Asn Thr Ala Pro Asp Arg Thr Arg Thr
            100                 105                 110
Leu Asp Phe Pro Pro Asn Ile Gln His Thr Leu
        115                 120
```

<210> SEQ ID NO 4
<211> LENGTH: 123
<212> TYPE: PRT
<213> ORGANISM: Macaca mulatta

<400> SEQUENCE: 4

```
Met Thr Asp Arg Asp Arg Trp Lys Lys Ser Thr Ser Leu Ser Asn Ser
1               5                   10                  15
Asp Thr Glu Met Lys Ser Glu Gln Leu Pro Pro Cys Val Asn Pro Gly
                20                  25                  30
Asn Pro Val Phe Ser Cys Met Leu Asp Pro Lys Thr Leu Gln Thr Ala
```

```
                35                  40                  45
Thr Ser Leu Ser Lys Pro Gln Gln Met Ile Met Tyr Lys Thr Asn Ser
         50                  55                  60
Ser His Tyr Gly Glu Phe Leu Pro Met Pro Gln Phe Phe Pro Cys Lys
 65                  70                  75                  80
Tyr Thr Pro Lys Glu Gln Val Phe Ser Ser His Ile Arg Ala Thr Gly
                 85                  90                  95
Phe Tyr Gln Asn Asn Thr Leu Asn Thr Ala Pro Asp Arg Thr Arg Thr
                100                 105                 110
Leu Asp Phe Pro Pro Asn Ile Gln His Thr Leu
            115                 120

<210> SEQ ID NO 5
<211> LENGTH: 123
<212> TYPE: PRT
<213> ORGANISM: Macaca fascicularis

<400> SEQUENCE: 5

Met Thr Asp Arg Asp Arg Trp Lys Lys Ser Thr Ser Leu Ser Asn Ser
 1               5                  10                  15
Asp Thr Glu Met Lys Ser Glu Gln Leu Pro Pro Cys Val Asn Pro Gly
                20                  25                  30
Asn Pro Val Phe Ser Cys Met Leu Asp Pro Lys Thr Leu Gln Thr Ala
                35                  40                  45
Thr Ser Leu Ser Lys Pro Gln Gln Met Ile Met Tyr Lys Thr Asn Ser
         50                  55                  60
Ser His Tyr Gly Glu Phe Leu Pro Met Pro Gln Phe Phe Pro Cys Lys
 65                  70                  75                  80
Tyr Thr Pro Lys Glu Gln Val Phe Ser Ser His Ile Arg Ala Thr Gly
                 85                  90                  95
Phe Tyr Gln Asn Asn Thr Leu Asn Thr Ala Pro Asp Arg Thr Arg Thr
                100                 105                 110
Leu Asp Phe Pro Pro Asn Ile Gln His Thr Leu
            115                 120

<210> SEQ ID NO 6
<211> LENGTH: 123
<212> TYPE: PRT
<213> ORGANISM: Equus caballus

<400> SEQUENCE: 6

Met Thr Glu Tyr Asp Gly Asp Lys Lys Ser Asn Ser Ala Ser Asn Ser
 1               5                  10                  15
Asp Thr Glu Met Lys Ala Glu Gln Leu Pro Pro Cys Val Asn Pro Gly
                20                  25                  30
Asn Pro Val Phe Ser Cys Met Leu Asp Pro Lys Thr Leu His Thr Ala
                35                  40                  45
Thr Ser Leu Ser Lys Pro Thr Thr Met Ile Met Tyr Lys Thr Asn Ser
         50                  55                  60
Gly Ser Tyr Gly Glu Phe Leu Pro Met Pro Gln Phe Phe Pro Cys Ile
 65                  70                  75                  80
Tyr Ser Pro Lys Glu Gln Val Phe Ser Ser His Ile Arg Ala Thr Gly
                 85                  90                  95
Phe Tyr Gln Asn Asn Thr Leu Asn Thr Ala Pro Asp Arg Thr Arg Thr
                100                 105                 110
Leu Asp Phe Pro Pro Asn Phe Gln His Thr Leu
```

-continued 115             120

<210> SEQ ID NO 7
<211> LENGTH: 123
<212> TYPE: PRT
<213> ORGANISM: Canis familiaris

<400> SEQUENCE: 7

Met Thr Glu Tyr Asp Trp Asp Lys Lys Cys Ala Ser Ala Ser Asp Ser
1               5                   10                  15

Gly Thr Glu Met Lys Pro Glu Gln Leu Pro Pro Cys Val Asn Pro Gly
            20                  25                  30

Asn Pro Val Phe Ser Cys Met Leu Asp Pro Lys Thr Leu Gln Thr Ala
        35                  40                  45

Thr Ser Leu Ser Lys Pro Lys Lys Met Ile Met Tyr Lys Thr Asn Ser
    50                  55                  60

Ser Asn Tyr Gly Glu Phe Leu Pro Met Pro Gln Phe Phe Pro Cys Asn
65                  70                  75                  80

Tyr Thr Pro Arg Glu Gln Val Phe Ser Ser Arg Ile Arg Ala Thr Gly
                85                  90                  95

Phe Tyr Gln Asn Asn Ser Leu Asn Ala Ala Pro Asp Arg Thr Arg Thr
            100                 105                 110

Leu Asp Phe Pro Pro Asn Leu Gln His Thr Leu
        115                 120

<210> SEQ ID NO 8
<211> LENGTH: 122
<212> TYPE: PRT
<213> ORGANISM: Bos taurus

<400> SEQUENCE: 8

Met Thr Glu Cys Asp Trp Glu Lys Lys Ser Thr Ser Ala Ser Asn Ser
1               5                   10                  15

Asp Thr Glu Met Lys Pro Glu Leu Pro Pro Cys Val Asn Pro Gly Asn
            20                  25                  30

Pro Val Phe Ser Cys Met Leu Asp Pro Lys Thr Leu His Thr Thr Thr
        35                  40                  45

Ser Leu Ser Lys Pro Lys Lys Met Ile Met Tyr Lys Thr Asn Ser Ser
    50                  55                  60

Asn Tyr Gly Glu Phe Leu Pro Met Pro Gln Phe Phe Pro Cys Tyr Tyr
65                  70                  75                  80

Thr Pro Arg Glu Gln Val Phe Ser Ser His Ile Arg Ala Thr Gly Phe
                85                  90                  95

Tyr Gln Asn Asn Thr Leu Asn Thr Ala Pro Asp Arg Thr Arg Thr Leu
            100                 105                 110

Asp Phe Pro Pro Asn Phe Gly His Thr Leu
        115                 120

<210> SEQ ID NO 9
<211> LENGTH: 123
<212> TYPE: PRT
<213> ORGANISM: Cricetulus griseus

<400> SEQUENCE: 9

Met Glu Lys Pro Thr Asp Trp Asp Leu Val Lys Lys Ser Thr Leu Thr
1               5                   10                  15

Ser Asp Glu Met Lys Pro Glu Pro Ser Ala Pro Cys Val Asn Pro Gly
            20                  25                  30

```
Asn Pro Val Phe Ser Cys Met Leu Asp Pro Lys Thr Phe His Thr Thr
            35                  40                  45

Thr Ser Leu Ser Lys Pro Gln Gln Met Ile Met Tyr Lys Thr Asn Ser
    50                  55                  60

Ser Gln Tyr Gly Ala Phe Ser Pro Lys Pro Gln Phe Phe Pro Cys Arg
65                  70                  75                  80

Tyr Thr Pro Lys Glu Gln Val Phe Ser Asn His Ile Lys Ala Thr Gly
                85                  90                  95

Phe Tyr Gln Asn Asn Ser Leu Asn Thr Ala Pro Asp Arg Thr Arg Thr
                100                 105                 110

Ile Asp Phe Pro Pro Asn Phe Gln His Thr Leu
            115                 120
```

<210> SEQ ID NO 10
<211> LENGTH: 155
<212> TYPE: PRT
<213> ORGANISM: Cavia porcellus

<400> SEQUENCE: 10

```
Met Asn Pro Gly Ser Cys Arg Ala Leu Ala Pro Gln Val Arg Thr Pro
1               5                   10                  15

Phe Leu Pro Gln Pro Phe Ser Ser Tyr Pro Leu Pro Thr Glu Ser Gln
                20                  25                  30

Ala His Gly Asn Pro Asp Gly Lys Arg Ser Ile Ser Ala Ala Gly Ser
            35                  40                  45

Asp Ala Glu Met Gln Ala Ala Arg Gln Pro Pro Cys Leu Ser Pro Gly
    50                  55                  60

Asn Pro Val Phe Ser Cys Met Leu Asp Pro Lys Thr Leu His Thr Ala
65                  70                  75                  80

Thr Ser Leu Ser Lys Pro Glu Glu Met Ile Met Tyr Lys Thr Ser Ala
                85                  90                  95

Gly Arg Tyr Gly Glu Phe Ser Pro Leu Pro Gln Phe Leu Pro Cys Ser
                100                 105                 110

Tyr Ile Pro Lys Glu Gln Gly Phe Ser Asn His Ile Arg Ala Thr Gly
            115                 120                 125

Leu Phe Gln Asn Asn Thr Leu Asn Thr Ala Leu Asp Arg Thr Arg Thr
    130                 135                 140

Ile Asp Phe Pro Pro Asn Phe Gln His Thr Leu
145                 150                 155
```

<210> SEQ ID NO 11
<211> LENGTH: 124
<212> TYPE: PRT
<213> ORGANISM: Rattus norvegicus

<400> SEQUENCE: 11

```
Met Ala Gly Glu Thr Asp Cys Asp Leu Asp Lys Lys Thr Ser Leu Thr
1               5                   10                  15

Ser Asp Ala Glu Met Arg Pro Glu Pro Pro Ala Pro Cys Ile Asn Pro
                20                  25                  30

Asp Asn Pro Val Phe Ser Cys Met Leu Asp Pro Lys Thr Leu His Thr
            35                  40                  45

Ser Thr Ser Leu Ser Lys Pro Gln Gln Met Ile Met Tyr Lys Thr Asn
    50                  55                  60

Ala Ser Gln Tyr Gly Ala Phe Ser Pro Arg Pro Tyr Phe Leu Pro Cys
65                  70                  75                  80
```

Lys Tyr Leu Pro Gln Glu Gln Met Phe Thr Glu His Leu Arg Ala Thr
                85                  90                  95

Gly Phe Tyr Gln Asn Asn Ser Leu Asn Ile Gly Pro Asp Arg Thr Arg
            100                 105                 110

Thr Val Asp Ser Pro Pro Asn Tyr Gln His Thr Leu
        115                 120

<210> SEQ ID NO 12
<211> LENGTH: 124
<212> TYPE: PRT
<213> ORGANISM: Mus musculus

<400> SEQUENCE: 12

Met Ala Arg Glu Thr Asp Cys Asp Leu Asp Lys Lys Thr Ser Leu Thr
1               5                   10                  15

Ser Asp Ala Glu Met Arg Pro Glu Pro Pro Ala Leu Cys Val Asn Pro
            20                  25                  30

Asp Asn Pro Val Phe Ser Cys Met Leu Asp Pro Lys Thr Leu His Thr
        35                  40                  45

Ala Thr Ser Leu Ser Lys Ala Gln Gln Met Ile Met Tyr Lys Thr Ser
    50                  55                  60

Ala Ser Gln Tyr Gly Ala Phe Ser Pro Arg Pro Phe Phe Leu Pro Cys
65                  70                  75                  80

Lys Phe Leu Pro Gln Glu Gln Ala Phe Thr Glu His Leu Lys Thr Thr
                85                  90                  95

Gly Phe Tyr Gln Asn Asn Ser Leu Asn Val Gly Pro Asp Arg Thr Arg
            100                 105                 110

Thr Ile Asp Ser Pro Pro Asn Tyr Gln His Thr Leu
        115                 120

<210> SEQ ID NO 13
<211> LENGTH: 78
<212> TYPE: PRT
<213> ORGANISM: Ornithorhynchus anatinus

<400> SEQUENCE: 13

Pro Pro Cys Val Asn Pro Gly Asn Pro Val Phe Ser Cys Met Leu Asp
1               5                   10                  15

Pro Lys Thr Leu Tyr Thr Ala Thr Ser Leu Ser Lys Pro Gln Gln Thr
            20                  25                  30

Ile Met Tyr Lys Thr Asn Ser Ser Asn Tyr Gly Glu Phe Leu Pro Lys
        35                  40                  45

Pro Gln Phe Phe Pro Cys Asn Tyr Thr Pro Arg Asp Gln Val Phe Ser
    50                  55                  60

Asn His Ile Arg Ala Thr Gly Phe Tyr Gln Asn Asn Ser Leu
65                  70                  75

<210> SEQ ID NO 14
<211> LENGTH: 127
<212> TYPE: PRT
<213> ORGANISM: Silurana tropicalis

<400> SEQUENCE: 14

Met Pro Lys Ala Ile Val Asn Gln Gln Glu Phe Gln Met Ser Arg Arg
1               5                   10                  15

Glu Leu Phe Ser Gly Asp Thr Glu Pro Ala Pro Ile Gly Arg Thr Cys
            20                  25                  30

```
Phe Asn Pro Gly Asn Pro Val Phe Ser Cys Met Leu Ala Pro Glu Asn
             35                  40                  45

Leu His Thr Ser Ser Leu Ser Lys Pro Gln Gln Thr Ile Met Tyr
 50                  55                  60

Lys Thr Thr Ser Ser Asp Tyr Gly Gly Leu Thr Pro Thr Ala Glu Cys
 65                  70                  75                  80

Leu Pro Arg Lys Tyr Phe Pro Lys Asp Gln Ser Phe Ser Lys Val Leu
             85                  90                  95

Arg Ala Ala Gly Met Phe Gln Asp Asn Ser Leu Asn Thr Glu Ile Asp
            100                 105                 110

Lys Gly Arg Val Cys Asp Val Ala Ala Asn Phe Gln His Thr Leu
            115                 120                 125

<210> SEQ ID NO 15
<211> LENGTH: 182
<212> TYPE: PRT
<213> ORGANISM: Tetraodon nigroviridis

<400> SEQUENCE: 15

Met Gly Cys Ala Leu Val Gly Gly Glu Gly Leu Val Ser Tyr Glu Leu
 1               5                  10                  15

Arg Glu Val Val Leu Pro Arg Gln Leu Gln Ala Lys Arg Asn Ile Gln
             20                  25                  30

Ser Ala Gly Trp Leu Ala Ser Glu Val Pro Gly Pro Val Ala Pro Arg
         35                  40                  45

Asn Pro Glu Lys Ala Arg Ser Ile Arg Pro Ala Ile Leu Leu Asn Met
 50                  55                  60

Thr Ser Val Gln Gln Thr Thr Pro Gly Ser Thr Ala Glu Lys Val Gln
 65                  70                  75                  80

Asp Lys Asn Val His Pro Cys Val Asn Pro Gly Asn Pro Val Phe Ser
             85                  90                  95

Cys Met Thr Thr Pro Val Ile Pro Thr Ser Tyr Met Phe Gln Ala Lys
            100                 105                 110

Gln Gln Gln Asn Ile Leu Phe Lys Thr Ser Ser Ser Glu Tyr Gly Ala
        115                 120                 125

Leu Arg Pro Thr Tyr Glu Thr Ala Pro Cys Ser His His Pro Val Ser
130                 135                 140

Gln Arg Phe Ser Gln His Leu Gly Gln Cys Gly Met Tyr Arg Asn His
145                 150                 155                 160

Ser Phe Asn Thr Met Ile Asp Arg Ser Arg Val His Asp Cys Pro Pro
                165                 170                 175

Asn Leu Gln Ser Thr Leu
            180

<210> SEQ ID NO 16
<211> LENGTH: 108
<212> TYPE: PRT
<213> ORGANISM: Branchiostoma floridae

<400> SEQUENCE: 16

Met Ser Ala Ala Gln Glu Gln Met Glu His Thr Val Lys Thr Cys Tyr
 1               5                  10                  15

Ser Pro Gly Asn Pro Val Phe Ser Cys Met Val Pro Thr Glu Lys
             20                  25                  30

Gly Thr Asn Tyr Ile Lys His Gln Gln Asn Leu Phe Tyr Arg Thr Thr
         35                  40                  45
```

```
Asn Gly Asp Tyr Gly His Leu Pro Ala Val Pro Glu Thr Thr Pro Leu
    50                  55                  60

Val Tyr His Pro Lys Ser Phe Lys Phe Ser Arg His Met Leu Met Tyr
65                  70                  75                  80

Gly Met His Arg Asp Asn Ser Leu Asn Thr Ala Ile Ser Arg Ser Arg
                85                  90                  95

Val Cys Asp Tyr Pro Pro Asn Leu Gln His Thr Leu
            100                 105
```

<210> SEQ ID NO 17
<211> LENGTH: 131
<212> TYPE: PRT
<213> ORGANISM: Saccoglossus kowalevskii

<400> SEQUENCE: 17

```
Met Ala Ala Asn Gly Glu Gln Val Val Glu Ser Gly Ala Glu Gln Ala
1               5                   10                  15

Lys Asn Thr Thr Thr Glu Pro Ile Met Val Thr Gln Asn Lys Asp Ala
            20                  25                  30

Glu Ile Leu Pro Val Arg Asp Leu Pro Cys Ala Asn Pro Gly Asn Pro
        35                  40                  45

Ile Phe Ser Cys Met Glu Arg Ile Arg Thr Pro Lys Glu Leu Gly Glu
    50                  55                  60

Trp Tyr Arg Glu Thr Pro Val Lys Pro Gln Gln Asn Pro Met Tyr Arg
65                  70                  75                  80

Thr Thr Asn Asp Thr Tyr Gly Gly Arg Val Pro Thr Val Glu Asp Met
                85                  90                  95

Pro Gln Thr Phe His Ala Lys Ser Gln Lys Phe Ser Glu His Leu Gly
            100                 105                 110

Val Cys Gly Met Tyr Arg Asn His Ser Leu Asn Thr Ala Leu Asp Gln
        115                 120                 125

Ser Lys Val
    130
```

<210> SEQ ID NO 18
<211> LENGTH: 137
<212> TYPE: PRT
<213> ORGANISM: Ciona intestinalis

<400> SEQUENCE: 18

```
Met Ala Gly Ala Glu Asn Lys Leu Thr Leu Pro His Glu Val Ile Asp
1               5                   10                  15

Asp Ser Gln Gln Tyr Pro Gln Glu Arg Thr Gly Glu Gln Ala Cys Asp
            20                  25                  30

Thr Asn Ala Ala Ser Leu Thr Glu Asn Met Pro Pro Cys Ala Ser Pro
        35                  40                  45

Gly Asn Pro Ile Phe Ser Cys Met Glu Arg Pro Thr Ile Glu Ala Pro
    50                  55                  60

Gln Gln Ser Asp Glu Gly Trp Phe Gly Tyr Gly Thr Lys Ser Gln
65                  70                  75                  80

Gln His Pro Met Tyr Arg Thr Thr Asn Ser Lys Tyr Tyr Gly Ser Met
                85                  90                  95
```

-continued

```
Pro Pro Ser Val His Thr Met Thr Ser Phe His Ala Arg Ser Gln Lys
            100                 105                 110

Phe Ser Glu Pro Leu Gly Lys Cys Gly Met Tyr Arg Asn Lys Gly Leu
        115                 120                 125

Asn Thr Gly Met Asp Gln Ser Lys Val
        130                 135
```